United States Patent [19]

Skuballa et al.

[11] Patent Number: 4,552,875
[45] Date of Patent: Nov. 12, 1985

[54] NOVEL CARBACYCLINAMIDES, THEIR PREPARATION AND USE AS MEDICINAL AGENTS

[75] Inventors: Werner Skuballa; Bernd Raduechel; Helmut Vorbrueggen, all of Berlin; Gerda Mannesmann, Cologne; Bob Nieuweboer; Michael H. Town, both of Berlin, all of Fed. Rep. of Germany

[73] Assignee: Schering Aktiengesellschaft, Berlin and Bergkamen, Fed. Rep. of Germany

[21] Appl. No.: 510,125

[22] Filed: Jul. 1, 1983

[30] Foreign Application Priority Data

Jul. 2, 1982 [DE]  Fed. Rep. of Germany ....... 3225287

[51] Int. Cl.[4] .................. C07C 177/00; A61K 31/557
[52] U.S. Cl. .................................. 514/234; 514/613; 544/176; 564/189
[58] Field of Search ................ 564/158, 159; 424/320; 544/176

[56] References Cited

U.S. PATENT DOCUMENTS

| | | | |
|---|---|---|---|
| 4,238,414 | 12/1980 | Morton, Jr. .................... | 564/453 |
| 4,306,075 | 12/1981 | Aristoff ......................... | 560/56 |
| 4,306,076 | 12/1981 | Nelson .......................... | 560/56 |
| 4,307,112 | 12/1981 | Gandolfi et al. ................ | 560/121 |
| 4,322,435 | 3/1982 | Kojima et al. .................. | 514/234 |
| 4,338,457 | 7/1982 | Aristoff ......................... | 560/119 |
| 4,346,041 | 8/1982 | Aristoff ......................... | 549/498 |
| 4,423,067 | 12/1983 | Skuballa ......................... | 424/305 |

FOREIGN PATENT DOCUMENTS

| | | |
|---|---|---|
| 2845770 | 4/1980 | Fed. Rep. of Germany . |
| 3048906 | 7/1982 | Fed. Rep. of Germany . |
| 2019847 | 2/1979 | United Kingdom . |
| 2017699 | 10/1979 | United Kingdom . |
| 2030144 | 2/1980 | United Kingdom . |
| 2070596 | 9/1981 | United Kingdom . |

OTHER PUBLICATIONS

European Search Report No. EP 83 73 0065, dated 07/09/83.

*Primary Examiner*—Robert Gerstl
*Attorney, Agent, or Firm*—Millen & White

[57] ABSTRACT

Carbacyclinamides of Formula I

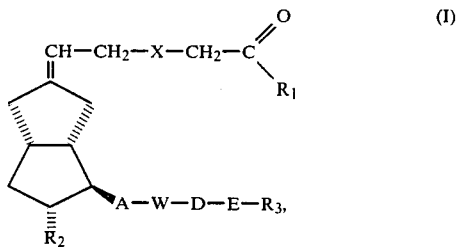

wherein
$R_1$ is $NHR_4$, wherein $R_4$ is H, $-(CH_2)_n-R_8$ or straight-chained or branched aliphatic groups of 1–10 carbon atoms, cycloalkyl of 3–10 carbon atoms, aryl, or lower mono- or polyhydroxyalkyl of 2–8 carbon atoms, or $R_1$ is $NR_4R_5$ wherein $R_4$ and $R_5$ each are straight-chained or branched, lower, mono- or polyhydroxyalkyl of 2–8 carbon atoms, or $R_4$ and $R_5$ together with the adjoining N-atom form a 5- or 6-membered heterocycle which can optionally contain additional hetero atoms and can be substituted; or $R_1$ is $NR_4R_5$ wherein $R_4$ is an aliphatic group of 1–10 carbon atoms, cycloalkyl of 3–10 carbon atoms, and $R_5$ is straight-chained or branched aliphatic group of 1–10 carbon atoms, cycloalkyl of 3–10 carbon atoms, aryl, or lower, mono- or polyhydroxyalkyl of 2–8 carbon atoms;
n is 1–4;
$R_8$ is $-CONH_2$ or $-N(C_1-C_4-alkyl)_2$;
$R_2$ is a free or functionally modified hydroxy group;
$R_3$ is aliphatic, cycloalkyl, optionally substituted aryl, or a heterocyclic group;
X is oxygen or $-CH_2-$;
A is $-CH_2-CH_2-$, trans$-CH=CH-$, or $-CH\equiv-$;
W is free or functionally modified hydroxymethylene or free or functionally modified $$\begin{matrix} CH_3 \\ -C- \\ OH \end{matrix}$$

wherein the OH-group can be in the α- or β-position;
D is

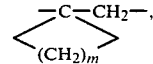

a straight-chain, saturated aliphatic group of 1–5 carbon atoms, or a branched, saturated or a straight-chain or branched, unsaturated aliphatic group of 2–5 carbon atoms, all of which groups can optionally be substituted by fluorine atoms;
m is 1–3;
E is a direct bond, $-C\equiv C-$, or $-CR_6=CR_7-$ wherein $R_6$ and $R_7$ are each a hydrogen atom or an alkyl group of 1–5 carbon atoms
have valuable pharmacological properties.

19 Claims, No Drawings

NOVEL CARBACYCLINAMIDES, THEIR PREPARATION AND USE AS MEDICINAL AGENTS

BACKGROUND OF THE INVENTION

The present invention concerns novel carbacyclinamides, a process for their preparation and their use as medicinal agents.

(5E)- and (5Z)-6a-carbaprostaglandin $I_2$ analogs are disclosed in German Unexamined Laid-Open Applications DOS Nos. 2,845,770; 2,900,352 (U.S. Pat. Nos. 4,322,435); 2,902,442 (U.S. Pat. Nos. 4,307,112); 2,904,655 (U.S. Pat. Nos. 4,238,414); 2,909,088; 3,209,702; 3,204,443; 3,048,906; and 2,912,409. The nomenclature of the compounds of this invention is based on a proposal by Morton and Brokaw (J. Org. Chem. 44: 2880 [1979]). The synthesis of these compounds yields in all cases two double-bond isomers characterized by the symbols (5E) or (5Z). The two isomers of this prototype are clarified by the following structural formulae:

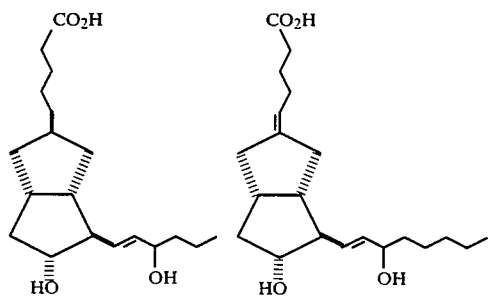

(5E)-6a-Carbaprostaglandin $I_2$  (5Z)-6a-Carbaprostaglandin $I_2$

It is known from the very voluminous state of the art of prostacyclins and their analogs that this class of compounds is suited, due to their biological and pharmacological properties, for the treatment of mammals, including man. The use of these compounds as medicinal agents, however, frequently meets with difficulties since their period of effectiveness is too short for therapeutic purposes. All structural modifications attempt to increase the duration of effectiveness as well as the selectivity of efficacy.

SUMMARY OF THE INVENTION

Accordingly, it is an object of this invention to provide new carbacyclins having such improved properties.

Upon further study of the specification and appended claims, further objects and advantages of this invention will become apparent to those skilled in the art.

These objects have been achieved by this invention by providing new carbacyclinamides of Formula I

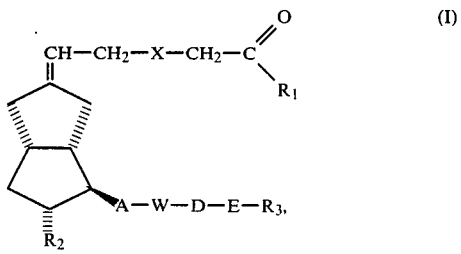

wherein $R_1$ is $NHR_4$, wherein $R_4$ is H, $-(CH_2)_n-R_8$ or straight-chained or branched aliphatic groups of 1-10 carbon atoms, cycloalkyl of 3-10 carbon atoms, aryl, or lower mono- or polyhydroxyalkyl of 2-8 carbon atoms; or $R_1$ is $NR_4R_5$ wherein $R_4$ and $R_5$ each are straight-chained or branched, lower mono- or polyhydroxyalkyl of 2-8 carbon atoms, or $R_4$ and $R_5$ together with the adjoining N-atom form a 5- or 6-membered heterocycle which can optionally contain additional hetero atoms and can be substituted; or $R_1$ is $NR_4R_5$ wherein $R_4$ is an aliphatic group of 1-10 carbon atoms, cycloalkyl of 3-10 carbon atoms, and $R_5$ is straight-chained or branched aliphatic group of 1-10 carbon atoms, cycloalkyl of 3-10 carbon atoms, aryl, or lower, mono- or polyhydroxyalkyl of 2-8 carbon atoms;

n is 1-4;

$R_8$ is $-CONH_2$ or $-N(C_1-C_4-alkyl)_2$;

$R_2$ is a free or functionally modified hydroxy group;

$R_3$ is aliphatic, cycloalkyl, optionally substituted aryl, or a heterocyclic group;

X is oxygen or $-CH_2-$;

A is $-CH_2-CH_2-$; trans-$CH=CH-$, or $-CH\equiv C-$;

W is free or frunctionally modified hydroxymethylene or free or functionally modified $$-\underset{\underset{OH}{|}}{\overset{\overset{CH_3}{|}}{C}}-$$

wherein the OH-group can be in the $\alpha$- or $\beta$-position;

D is $$=C-CH_2-, \atop (CH_2)_m$$

a straight-chain, saturated aliphatic group of 1-5 carbon atoms, or a branched, saturated or a straight-chain or branched, unsaturated aliphatic group of 2-5 carbon atoms, all of which groups can optionally be substituted by fluorine atoms;

m is 1-3;

E is a direct bond, $-C\equiv C-$, or $-CR_6=CR_7-$ wherein $R_6$ and $R_7$ are each a hydrogen atom or an alkyl group of 1-5 carbon atoms.

It has now been found that the amides of carbacyclins of this invention possess a markedly longer effect than the free acids of the carbacyclin derivatives. The compounds of this invention have bronchodilatory effects and are suitable for inhibition of thrombocyte aggregation, for lowering blood pressure by way of vasodilation, and for inhibiting gastric acid secretion.

DETAILED DISCUSSION

The compounds of Formula I include (5E)- as well as (5Z)-isomers.

The residues $R_4$ and $R_5$, as straight-chained or branched, lower, mono- or polyhydroxyalkyl residues, contain 2–8 carbon atoms, preferably 2–5 carbon atoms. Straight-chain residues $R_4$ and $R_5$ preferably contain 2–4 carbon atoms and branched residues preferably contain 3–5 carbon atoms. The hydroxy groups in $R_4$ and $R_5$ can be present as primary or secondary hydroxy groups. The residues $R_4$ and $R_5$ can contain 1–5 hydroxy groups; 1–3 hydroxy groups are preferred. Examples of such residues $R_4$ and $R_5$ include: 2-hydroxyethyl, 2-hydroxypropyl, 3-hydroxypropyl, 2-hydroxy-1-methylpropyl, 3-hydroxy-1-methylpropyl, 1-(hydroxymethyl)ethyl, 2-hydroxybutyl, 3-hydroxybutyl, 4-hydroxybutyl, 2-hydroxy-1-methylbutyl, 3-hydroxy-1-methylbutyl, 4-hydroxy-1-methylbutyl, 3-hydroxy-2-methylbutyl, 4-hydroxy-2-methylbutyl, 2-hydroxyisobutyl, 3-hydroxyisobutyl, 2-hydroxy-1,1-dimethylethyl, 3-hydroxy-1,1-dimethylpropyl, 2,3-dihydroxypropyl, 2,3-dihydroxybutyl, 2,4-dihydroxybutyl, 3,4-dihydroxybutyl, 3-hydroxy-2-(hydroxymethyl)propyl, 2,3-dihydroxy-1-methylpropyl, 2-hydroxy-3-(hydroxymethyl)butyl, 2,3,4-trihydroxybutyl, 2,4-dihydroxy-3-(hydroxymethyl)butyl, 3-hydroxy-2,2-bis(hydroxymethyl)propyl, 4-hydroxy-3,3-bis(hydroxymethyl)butyl, 4-hydroxy-2,2-bis(hydroxymethyl)butyl, 2-hydroxy-1,1-bis(hydroxymethyl)ethyl, and glucosamine.

When the residue

represents a heterocyclic ring, the residues $R_4$ and $R_5$ jointly form a bivalent, saturated hydrocarbon residue of 4 or 5 members which latter can be replaced by additional hetero atoms, such as —O—, —S— or —N—, usually one such additional hetero atom. These heterocyclic rings can also be substituted (e.g., by $C_{1-4}$-alkyl), preferably on an additional N atom. Suitable bivalent residues include: —CH$_2$—CH$_2$—O—CH$_2$—CH$_2$—, —(CH$_2$)$_4$—, —(CH$_2$)$_5$—, —CH$_2$—CH$_2$S—CH$_2$—CH$_2$—, —CH$_2$—CH$_2$—NH—CH$_2$—CH$_2$—, —CH$_2$—CH$_2$—N(C$_1$-C$_4$-alkyl)—CH$_2$—CH$_2$—, —CH$_2$—NH—CH$_2$—CH$_2$—, —CH$_2$—N(C$_1$-C$_4$-alkyl)—CH$_2$—CH$_2$—, —CH$_2$—S—CH$_2$—CH$_2$—, —CH$_2$—O—CH$_2$—CH$_2$—, etc.

The hydroxy groups $R_2$ and in W can be functionally modified, for example by conventional etherification or esterification, wherein the free or modified hydroxy groups in W can be in the α- or β-position, free hydroxy groups being preferred.

The many suitable ether and acyl residues are well known to persons skilled in the art. Readily cleavable ether residues are preferred, such as, for example, the tetrahydropyranyl, tetrahydrofuranyl, α-ethoxyethyl, trimethylsilyl, dimethyl-tert-butylsilyl, and tribenzylsilyl residues. Suitable acyl residues are also well known to persons skilled in the art; examples which can be mentioned are acetyl, propionyl, butyryl, benzoyl, etc., e.g., $C_{1-15}$-hydrocarbon carboxylic or sulfonic acid based acyl groups.

The aliphatic groups $R_3$, $R_4$, and $R_5$ include straight-chained and branched, saturated and unsaturated residues, preferably saturated ones, (i.e., alkyl groups) of 1–10, especially 1–7 carbon atoms, and including $C_{2-10}$-alkenyl groups, all of which can, optionally, be substituted by optionally substituted aryl as described below for $R_4$ per se. Examples include methyl, ethyl, propyl, butyl, isobutyl, tert-butyl, pentyl, hexyl, heptyl, octyl, butenyl, isobutenyl, propenyl, pentenyl, hexenyl, benzyl, phenethyl, 1-phenylethyl, and p-chlorobenzyl. $R_6$, $R_7$ and $R_8$ alkyl groups include those described above.

The cycloalkyl groups for $R_3$, $R_4$, and $R_5$, each can contain 3–10, preferably 3–6 carbon atoms in the ring. The rings can be substituted by alkyl groups of 1–4 carbon atoms. Examples include cyclopropyl, cyclobutyl, cyclopentyl, cyclohexyl, methylcyclohexyl, and adamantyl.

Examples of suitable substituted and unsubstituted aryl groups $R_3$, $R_4$ and $R_5$, include: phenyl, 1-naphthyl and 2-naphthyl, (i.e., $C_{6-10}$-aryl), each of which can be substituted by 1–3 halogen atoms, a phenyl group, 1–3 alkyl groups of respectively 1–4 carbon atoms, or a chloromethyl, fluoromethyl, trifluoromethyl, carboxy, $C_1$-$C_4$-alkoxy, or hydroxy group. Substitution in the 3- and 4-positions on the phenyl ring is preferred, for example by fluorine, chlorine, $C_1$-$C_4$-alkoxy, or trifluoromethyl, or in the 4-position by hydroxy.

Suitable heterocyclic groups $R_3$ include 5- and 6-membered heterocycles containing at least one hetero atom, preferably nitrogen, oxygen, or sulfur, usually one such atom. The rings are usually aromatic. Examples include 2-furyl, 2-thienyl, 2-pyridyl, 3-pyridyl, 4-pyridyl, 4-furyl, 3-thienyl, etc.

The aliphatic group D can be straight-chain, saturated alkylene of 1–5 carbon atoms or branched-chain, saturated or straight-chain or branched, unsaturated (alkenylene) residues of 2–5 carbon atoms, which can optionally be substituted by fluorine atoms, 1,2-methylene

or 1,1-trimethylene

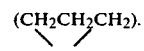

Examples include: methylene, fluoromethylene, ethylene, 1,2-propylene, ethylethylene, trimethylene, tetramethylene, pentamethylene, 1-methyltetramethylene, 1-methyltrimethylene, 1,1-trimethylenethylene etc.

Especially preferred compounds of this invention are those wherein E is —C≡C— or —CR$_6$=CR$_7$—, wherein both residues $R_6$ and $R_7$ represent an alkyl group of 1–5 carbon atoms; wherein the lower chain has a 16-methyl substitution, and wherein the upper chain has a mono- or polyhydroxyalkylamide group in the 1-position.

This invention furthermore relates to a process for the preparation of the carbacyclinamides of Formula I, comprising, conventionally reacting a compound of Formula II

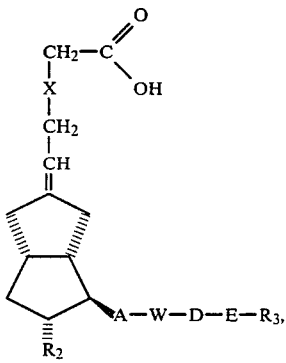

(II)

wherein $R_2$, $R_3$, X, A, W, D, and E are as defined above, optionally after blockage of free hydroxy groups, with amines of Formula III

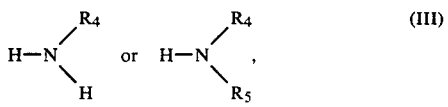

(III)

wherein $R_4$ and $R_5$ are as defined above, after a preceding reaction with the isobutyl ester of chloroformic acid in the presence of a tertiary amine; and, optionally, subsequently, liberating blocked hydroxy groups, esterifying or etherifying free hydroxy groups and/or separating the compounds into isomers.

The reaction of the compound of Formula II with an amine of Formula III is conducted at temperatures of −60° to 60° C., preferably 10°–40° C., in an inert solvent, for example acetone, acetonitrile, dimethylacetamide, dimethylformamide, or dimethylsulfoxide. Suitable bases for the preparation of the intermediary anhydrides are well known to persons skilled in the art for such amidations, preferably tertiary bases, e.g., triethylamine, trimethylamine, tributylamine, trioctylamine, pyridine, N,N-diethylisopropylamine, etc.

The compounds of Formula II are known from the aforementioned German unexamined laid-open applications. The compounds of Formula III are known from the literature. That is, all starting materials are known or readily preparable using fully conventional methods.

The functional modification of the free OH-groups takes place by means of methods known to those skilled in the art. For example, in order to introduce the ether blocking groups, the reaction can be carried out with dihydropyran in methylene chloride or chloroform using an acidic condensation agent, e.g., p-toluenesulfonic acid. Dihydropyran is used in excess, preferably in 4- to 10-times the amount theoretically required. The reaction is normally completed at 0°–30° C. after 15–30 minutes.

The acyl blocking groups can be introduced by conventionally reacting a compound of Formula I with a carboxylic acid derivative, e.g., an acid chloride, acid anhydride, etc.

The liberation of a functionally modified OH-group to obtain the compounds of formula I also takes place according to methods known per se. For example, ether blocking groups can be split off in an aqueous solution of an organic acid, e.g., acetic acid, propionic acid, etc., or in an aqueous solution of an inorganic acid, e.g., hydrochloric acid. To improve solubility, a water-miscible, inert organic solvent is suitably added. Organic solvents that can be used are, for example, alcohols, such as methanol and ethanol, and ethers, such as dimethoxyethane, dioxane, and tetrahydrofuran. Tetrahydrofuran is preferably employed. The splitting-off step is preferably carried out at temperatures of 20° to 80° C.

The silyl ether blocking groups can be split off, for example, with tetrabutylammonium fluoride. Examples of suitable solvents are tetrahydrofuran, diethyl ether, dioxane, methylene chloride, etc. The splitting-off process is preferably conducted at temperatures of 0° to 80° C.

The acyl groups can be saponified, for example, with alkali metal or alkaline earth metal carbonates or hydroxides in an alcohol or in the aqueous solution of an alcohol. Aliphatic alcohols can be utilized in this connection, e.g., methanol, ethanol, butanol, etc., preferably methanol. Worth mentioning as the alkali metal carbonates and hydroxides are potassium and sodium salts, but the potassium salts are preferred. Examples of suitable alkaline earth metal carbonates and hydroxides include calcium carbonate, calcium hydroxide, and barium carbonate. The reaction takes place at −10° to 70° C., preferably at 25° C.

The compounds of this invention have blood-pressure-lowering and bronchodilatory effects. They are furthermore suitable for inhibiting thrombocyte aggregation. Consequently, the novel carbacyclin derivatives of Formula I represent valuable pharmaceutically active agents. Moreover, with a similar spectrum of activity, they exhibit a higher specificity as compared with corresponding prostacyclins and, above all, an essentially longer efficacy. As compared with $PGI_2$, they are distinguished by higher stability.

The high tissue specificity of the novel carbacyclinamides is demonstrated in a study on smooth-muscle organs, such as, for example, on the guinea pig ileum or on the isolated rabbit trachea, where substantially lower stimulation can be observed than in the administration of natural prostaglandins of the E-, A-, or F-type.

The novel carbacyclin analogs exhibit the properties typical for prostacyclins, such as, for example, lowering of peripheral arterial and coronary vascular resistance, inhibition of thrombocyte aggregation and dissolution of platelet thrombi, myocardial cytoprotection and thus lowering of systemic blood pressure without simultaneously lowering stroke volume and coronary blood flow; treatment for strokes, prophylaxis and therapy of coronary heart disease, coronary thrombosis, cardiac infarction, peripheral arterial diseases, arteriosclerosis and thrombosis, prophylaxis and therapy of ischemic attacks of the CNS system, therapy for shock, inhibition or bronchoconstriction, inhibition of gastric acid secretion, cytoprotection for gastric and intestinal mucosa, cytoprotection in liver and pancreas, antiallergic properties, lowering of pulmonary vascular resistance and pulmonary blood pressure, promotion of kidney blood flow, utilization in place of heparin or as adjuvant in dialysis of hemofiltration, preservation of blood plasma stores, especially blood platelet stores, inhibition of labor, treatment of gestational toxicosis, enhancement of cerebral blood flow, etc. In addition, the novel carbacyclin derivatives exhibit antiproliferative and antidiarrheogenic properties. The carbacyclins of this invention also can be utilized in combination, for example, with β-blockers or diuretics.

The novel prostaglandin analogs of this invention are substantially more selective with regard to potency, as compared with known prostaglandin analogs in causing prostaglandin-like biological responses, and have a substantially longer duration of biological activity. Accordingly, each of these novel prostaglandin analogs is surprisingly and unexpectedly more useful than one of the corresponding conventional prostaglandin-type compounds for at least one of the pharmacological purposes indicated above, because it has a different and narrower spectrum of biological potency than the known prostaglandin, and therefore is more specific in its acitivity and causes smaller and fewer undesired side effects than when the prostaglandin is used for the same purpose. Moreover, because of its prolonged activity, fewer and smaller doses of the novel prostaglandin analog are frequently effective in attaining the desired result.

The dosage of the compounds is usually 1–1,500 $\mu$g/kg/day when administered to human patients. The unit dosage for the pharmaceutically acceptable carrier is usually 0.01–100 mg. Precise dosages in a given case can be readily determined using fully conventional methods, e.g., by differential potency tests vis a vis a known analogous agent such as $PGI_2$. In general, the administration of the compounds of this invention will be analogous to that of a related known agent e.g., $PGI_2$.

Upon systemic administration, the novel carbacyclinamides show a markedly prolonged efficacy, for example as compared with the free acids.

The active agents of this invention can serve, in conjunction with the auxiliary agents known and customary in galenic pharmacy, for example for the production of blood-pressure-lowering drugs. Thus, the invention also concerns medicinal agents based on the compounds of Formula I and conventional auxiliary agents and excipients.

The pharmacologically active compounds of this invention can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(5E)-(16RS)-16-Methyl-18,18,19,19-tetradehydro-6a-carbaprostaglandin $I_2$ (2,3-Dihydroxypropyl)amide 333 mg of (5E)-(16RS)-16-methyl-18,18,19,19-tetradehydro-6a-carbaprostaglandin $I_2$ 11,15-bistetrahydropyranyl ether is dissolved in 4 ml of acetone and combined at 0° C. with 74 mg of triethylamine and 100 mg of isobutyl chloroformate. The mixture is stirred for 20 minutes and then a solution of 574 mg of 1-amino-2,3-dihydroxypropane in 9 ml of acetone and 9 ml of acetonitrile is added thereto; the mixture is agitated for one hour at 24° C. Subsequently, the mixture is concentrated under vacuum, the residue is taken up in 100 ml of methylene chloride, shaken three times with brine, dried over magnesium sulfate, and evaporated under vacuum.

The residue is agitated for 18 hours at 24° C. with 10 ml of a mixture of acetic acid, water, tetrahydrofuran (65:35:10), evaporated under vacuum, and the remainder is purified by column chromatography on silica gel. With methylene chloride/isopropanol (8+2), 205 mg of the title compound is obtained as a colorless oil.

IR ($CHCl_3$): 3660, 3380, 2925, 1640, 970 cm$^{-1}$.

EXAMPLE 2

(5E)-(16RS)-16-Methyl-18,18,19,19-tetradehydro-6a-carbaprostaglandin $I_2$ Amide Obtained analogously to Example 1 from 400 mg of (5E)-(16RS)-methyl-18,18,19,19-tetradehydro-6a-carbaprostaglandin $I_2$ 11,15-bistetrahydropyranyl ether in 7.1 ml of tetrahydrofuran, triethylamine, and isobutyl ester of chloroformic acid. At 0° C., ammonia is introduced into the solution for 10 minutes until saturation, and the solution is allowed to stand at room temperature for one hour. The product is worked up analogously to Example 1. Yield: 447 mg, of which 216 mg is further processed. The tetrahydropyranyl blocking groups are split off as set forth in Example 1. Yield: 200 mg of the title compound as an oil.

IR ($CHCl_3$): 3600, 3400 (broad), 2920, 1680, 1590, 968 cm$^{-1}$.

EXAMPLE 3

(5E)-(16RS)-16-Methyl-18,18,19,19-tetradehydro-6a-carbaprostaglandin $I_2$ (2-Hydroxyethyl)amide Produced analogously to Example 1 from 500 mg of (5E)-(16RS)-16-methyl-18,18,19,19-tetradehydro-6a-carbaprostaglandin $I_2$ 11,15-bistetrahydropyranyl ether in 4.5 ml of acetone, triethylamine, and isobutyl chloroformate. A solution of 577.2 mg of 2-aminoethanol in 13.5 ml of acetone and 13.5 ml of acetonitrile is added dropwise to the reaction mixture. Yield: 586 mg, of which 300 mg is further processed. Splitting off of the tetrahydropyranyl blocking groups takes place analogously to Example 1. Yield: 122 mg of the title compound as an oil.

IR (CHCl$_3$): 3600, 3350 (broad), 2930, 1658, 1515, 968 cm$^{-1}$.

EXAMPLE 4

(5E)-(16RS)-16-Methyl-18,18,19,19-tetradehydro-6a-carbaprostaglandin I$_2$ (2-Diethylaminoethyl)amide Obtained analogously to Example 1 from 316 mg of (5E)-(16RS)-16-methyl-18,18,19,19-tetradehydro-6a-carbaprostaglandin I$_2$ 11,15-bistetrahydropyranyl ether in 3 ml of acetone, triethylamine, and isobutyl chloroformate. A solution of 695 mg of 2-diethylaminoethylamine in 16.2 ml of acetone/10.8 ml of acetonitrile is added dropwise to the reaction mixture. Yield: 324 mg, of which 310 mg is further processed. The tetrahydropyranyl blocking groups are split off analogously to Example 1. Yield: 168.4 mg of the title compound as an oil.

IR (CHCl$_3$): 3600, 3400 (broad), 2963, 2925, 1655, 1602, 970 cm$^{-1}$.

EXAMPLE 5

(5E)-(16RS)-16-Methyl-18,18,19,19-tetradehydro-6a-carbaprostaglandin I$_2$ (2,3,4-Trihydroxybutyl)amide Produced analogously to Example 1 from (5E)-(16RS)-16-methyl-18,18,19,19-tetradehydro-6a-carbaprostaglandin I$_2$ 11,15-bistetrahydropyranyl ether and 2,3,4-trihydroxybutylamine.

IR (CHCl$_3$): 3600, 3380 (broad), 2930, 1670, 1585, 970 cm$^{-1}$.

EXAMPLE 6

(5E)-(16RS)-16-Methyl-18,18,19,19-tetradehydro-6a-carbaprostaglandin I$_2$ Glucosamide Prepared analogously to Example 1 from (5E)-(16RS)-16-methyl-18,18,19,19-tetradehydro-6a-carbaprostaglandin I$_2$ 11,15-bistetrahydropyranyl ether and glucosamine.

IR (CHCl$_3$): 3600, 3400 (broad), 2925, 1680, 1585, 965 cm$^{-1}$.

EXAMPLE 7

(5E)-(16RS)-16-Methyl-3-oxa-18,18,19,19-tetradehydro-6a-carbaprostaglandin I$_2$ (2,3-Dihydroxypropyl)amide Obtained analogously to Example 1 from (5E)-(16RS)-16-methyl-3-oxa-18,18,19,19-tetradehydro-6a-carbaprostaglandin I$_2$ 11,15-bistetrahydropyranyl ether and 1-amino-2,3-dihydroxypropane.

IR (CHCl$_3$): 3600, 3400 (broad), 2930, 1690, 1580, 960 cm$^{-1}$.

EXAMPLE 8

(5E)-(16RS)-13,14-Didehydro-16-methyl-18,18,19,19-tetradehydro-6a-carbaprostaglandin I$_2$ (2,3-Dihydroxypropyl)amide Obtained as set forth in Example 1 from (5E)-(16RS)-13,14-didehydro-16-methyl-18,18,19,19-tetradehydro-6a-carbaprostaglandin I$_2$ 11,15-bistetrahydropyranyl ether and 1-amino-2,3-dihydroxypropane.

IR (CHCl$_3$): 3600, 3390 (broad), 2925, 1680, 1575, 965 cm$^{-1}$.

EXAMPLE 9

(5E)-18,18,19,19-Tetradehydro-16,16-trimethylene-6a-carbaprostaglandin I$_2$ (2,3-Dihydroxypropyl)amide Obtained analogously to Example 1 from (5E)-18,18,19,19-tetradehydro-16,16-trimethylene-6a-carbaprostaglandin I$_2$ 11,15-bistetrahydropyranyl ether and 1-amino-2,3-dihydroxypropane.

IR (CHCl$_3$): 3600, 3410 (broad), 2930, 1690, 1585, 975 cm$^{-1}$.

EXAMPLE 10

(5E)-16,16-Dimethyl-18,18,19,19-tetradehydro-6a-carbaprostaglandin I$_2$ (2,3-Dihydroxypropyl)amide Analogously to Example 1 from (5E)-16,16-dimethyl-18,18,19,19-tetradehydro-6a-carbaprostaglandin I$_2$ 11,15-bistetrahydropyranyl ether and 1-amino-2,3-dihydroxypropane.

IR (CHCl$_3$): 3600, 3400 (broad), 2930, 1690, 1580, 965 cm$^{-1}$.

EXAMPLE 11

(5E)-(16RS)-16,20-Dimethyl-18,18,19,19-tetradehydro-6a-carbaprostaglandin I$_2$ (2,3-Dihydroxypropyl)amide Produced as set forth in Example 1 from (5E)-(16RS)-16,20-dimethyl-18,18,19,19-tetradehydro-6a-carbaprostaglandin I$_2$ 11,15-bistetrahydropyranyl ether and 1-amino-2,3-dihydroxypropane.

IR (CHCl$_3$): 3600, 3390 (broad), 2925, 1680, 1575, 970 cm$^{-1}$.

EXAMPLE 12

(5E)-20-Methyl-18,18,19,19-tetradehydro-16,16-trimethylene-6a-carbaprostaglandin I$_2$ (2,3-Dihydroxypropyl)amide Obtained analogously to Example 1 from (5E)-20-methyl-18,18,19,19-tetradehydro-16,16-trimethylene-6a-carbaprostaglandin I$_2$ 11,15-bistetrahydropyranyl ether and 1-amino-2,3-dihydroxypropane.

IR (CHCl$_3$): 3600, 3410 (broad), 2930, 1685, 1570, 965 cm$^{-1}$.

EXAMPLE 13

(5E)-13,14-Didehydro-20-methyl-18,18,19,19-tetradehydro-16,16-trimethylene-6a-carbaprostaglandin I$_2$ (2,3-Dihydroxypropyl)amide Produced analogously to Example 1 from (5E)-13,14-didehydro-20-methyl-18,18,19,19-tetradehydro-16,16-trimethylene-6a-carbaprostaglandin I$_2$ 11,15-bistetrahydropyranyl ether and 1-amino-2,3-dihydroxypropane.

IR (CHCl$_3$): 3600, 3410 (broad), 2920, 1680, 1585, 975 cm$^{-1}$.

EXAMPLE 14

(5E)-(16RS)-16,19-Dimethyl-18,19-didehydro-6a-carbaprostaglandin I$_2$ (2,3-Dihydroxypropyl)amide Obtained analogously to Example 1 from (5E)-(16RS)-16,19-dimethyl-18,19-didehydro-6a-carbaprostaglandin I$_2$ 11,15-bistetrahydropyranyl ether and 1-amino-2,3-dihydroxypropane.

IR (CHCl$_3$): 3600, 3390 (broad), 2915, 1690, 1580, 965 cm$^{-1}$.

EXAMPLE 15

(5E)-(16RS)-16-Methyl-18,18,19,19-tetradehydro-6a-carbaprostaglandin I$_2$ Morpholide Obtained analogously to Example 1 from 265 mg of (5E)-(16RS)-16-methyl-18,18,19,19-tetradehydro-6a-carbapostaglandin I$_2$ 11,15-bistetrahydropyranyl ether and 365 mg of morpholine. Yield: 282 mg (94.3% of theory), of which 241 mg is further processed. The tetrahydropyranyl blocking groups are split off analogously to Example 1. Yield: 130 mg (75.1% of theory) of the title compound as an oil.

IR (CHCl$_3$): 3600, 3420 (broad), 2920, 2860, 1630, 968 cm$^{-1}$.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. A carbacyclinamide of the formula

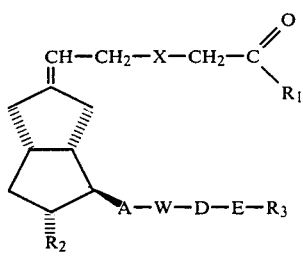

wherein

R$_1$ is NHR$_4$, wherein R$_4$ is (a) -(CH$_2$)$_n$-R$_8$, (b) C$_{2-10}$-alkenyl, (c) C$_{1-10}$-alkyl or C$_{2-10}$-alkenyl each substituted by C$_{6-10}$-aryl or by C$_{6-10}$-aryl substituted by 1-3 halogen atoms, a phenyl group, 1-3 C$_{1-4}$ alkyl groups or a chloromethyl, fluoromethyl, trifluoromethyl, carboxy, hydroxy or C$_{1-4}$ alkoxy group; (d) C$_{3-10}$-cycloalkyl, (e) C$_{3-10}$-cycloalkyl substituted by C$_{1-4}$-alkyl, (f) C$_{6-10}$-aryl, (g) C$_{6-10}$-aryl substituted by 1-3 halogen atoms, a phenyl group, 1-3 C$_{1-4}$-alkyl groups or a chloromethyl, fluoromethyl, trifluoromethyl, carboxy, hydroxy or C$_{1-4}$ alkoxy group; or (h) C$_{2-8}$-alkyl substituted by 1-5 hydroxy groups, or R$_1$ or NR$_4$R$_5$, wherein R$_4$ and R$_5$ each is C$_{2-8}$-alkyl substituted by 1-5 hydroxy groups or R$_4$ and R$_5$ together with the adjoining N-atom form a 5- or 6-membered heterocycle containing up to 1 additional O, S or N atom wherein an additional N-atom can be substituted by C$_{1-4}$-alkyl, or R$_1$ is NR$_4$R$_5$ wherein R$_4$ is (a) C$_{1-10}$-alkyl, (b) C$_{2-10}$-alkenyl, (c) C$_{1-10}$-alkyl or C$_{2-10}$-alkenyl each substituted by C$_{6-10}$-aryl or C$_{6-10}$-aryl substituted by 1-3 halogen atoms, a phenyl group, 1-3 C$_{1-4}$ alkyl groups or a chloromethyl, fluoromethyl, trifluoromethyl, carboxy, hydroxy or C$_{1-4}$-alkoxy group; (d) C$_{3-10}$-cycloalkyl or (e) C$_{3-10}$-cycloalkyl substituted by C$_{1-4}$-alkyl, and R$_5$ is (a) C$_{2-10}$-alkenyl, (b) C$_{1-10}$-alkyl or C$_{2-10}$-alkenyl each substituted by C$_{6-10}$-aryl or by C$_{6-10}$-aryl substituted by 1-3 halogen atoms, a phenyl group, 1-3 C$_{1-4}$ alkyl groups or a chloromethyl, fluoromethyl, trifluoromethyl, carboxy, hydroxy or C$_{1-4}$-alkoxy group; (c) C$_{3-10}$-cycloalkyl, (d) C$_{3-10}$-cycloalkyl substituted by C$_{1-4}$-alkyl, (e) C$_{6-10}$-aryl, (f) C$_{6-10}$-aryl substituted by 1-3 halogen atoms, a phenyl group, 1-3 C$_{1-4}$ alkyl groups or a chloromethyl, fluoromethyl, trifluoromethyl, carboxy, hydroxy or C$_{1-4}$-alkoxy group; or (g) C$_{2-8}$-alkyl substituted by 1-5 hydroxy groups, N is 1-4;

R$_8$ is —CONH$_2$ or —N(C$_1$-C$_4$-alkyl)$_2$;

R$_2$ is OR:

R$_3$ is (a) C$_{1-10}$-alkyl, (b) C$_{2-10}$-alkenyl, (c) C$_{1-10}$-alkyl or C$_{2-10}$-alkenyl each substituted by C$_{6-10}$-aryl or by C$_{6-10}$-aryl substituted by 1-3 halogen atoms, a phenyl group, 1-3 C$_{1-4}$ alkyl groups or a chloromethyl, fluoromethyl, trifluoromethyl, carboxy, hydroxy or C$_{1-4}$ alkoxy group; (d) C$_{3-10}$-cycloalkyl, (e) C$_{3-10}$-cycloalkyl substituted by C$_{1-4}$-alkyl, (f) C$_{6-10}$-aryl, (g) C$_{6-10}$-aryl substituted by 1-3 halogen atoms, a phenyl group, 1-3 C$_{1-4}$ alkyl groups or a chloromethyl, fluoromethyl, trifluoromethyl, carboxy, hydroxy or C$_{1-4}$ alkoxy group; or (h) an aromatic heterocycle of 5 or 6 ring atoms one of which is O, N or S, the remainder being carbon atoms;

X is —O— or —CH$_2$—;

A-W-D-E-R$_3$ is

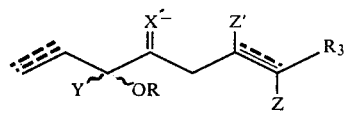

Y is H or CH$_3$;

represents an α- or β-bond; ≡≡≡≡≡ represents a single, double or triple bond, the double bond in the 13-position being in the trans-configuration;

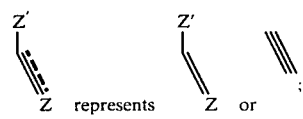

=X$^-$ is H, C$_{1-3}$-alkyl; C$_{1-3}$-dialkyl; H, H; H, F; or

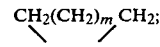

Z and Z' each is H or C$_{1-5}$-alkyl;

m is 1-3; and

R is H, tetrahydropyranyl, tetrahydrofuranyl, α-ethoxyethyl, trimethylsilyl, dimethyl-tert-butylsilyl, tribenzylsilyl or an acyl group of a C$_{1-15}$-hydrocarbon carboxylic or sulfonic acid.

2. A compound of claim 1 wherein =X' is H, CH$_3$; CH$_3$,CH$_3$; H, H; or

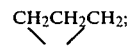

and Z and Z' are H or CH$_3$.

3. A compound of claim 1 wherein R$_1$ is NH(hydroxyalkyl).

4. (5E)-(16RS)-16-Methyl-18,18,19,19-tetradehydro-6a-carbaprostaglandin $I_2$ (2,3-dihydroxypropyl)amide, a compound of claim 1.

5. (5E)-(16RS)-16-Methyl-18,18,19,19-tetradehydro-6a-carbaprostaglandin $I_2$ (2-hydroxyethyl)amide, a compound of claim 1.

6. (5E)-(16RS)-16-Methyl-18,18,19,19-tetradehydro-6a-carbaprostaglandin $I_2$ (2-diethylaminoethyl)amide, a compound of claim 1.

7. (5E)-(16RS)-16-Methyl-18,18,19,19-tetradehydro-6a-carbaprostaglandin $I_2$ (2,3,4-trihydroxybutyl)amide, a compound of claim 1.

8. (5E)-(16RS)-16-Methyl-18,18,19,19-tetradehydro-6a-carbaprostaglandin $I_2$ glucosamide, a compound of claim 1.

9. (5E)-(16RS)-16-Methyl-3-oxa-18,18,19,19-tetradehydro-6a-carbaprostaglandin $I_2$ (2,3-dihydroxypropyl)amide, a compound of claim 1.

10. (5E)-(16RS)-13,14-Didehydro-16-methyl-18,18,19,19-tetradehydro-6a-carbaprostaglandin $I_2$ (2,3-dihydroxypropyl)amide, a compound of claim 1.

11. (5E)-18,18,19,19-Tetradehydro-16,16-trimethylene-6a-carbaprostaglandin $I_2$ (2,3-dihydroxypropyl)amide, a compound of claim 1.

12. (5E)-16,16-Dimethyl-18,18,19,19-tetradehydro-6a-carbaprostaglandin $I_2$ (2,3-dihydroxypropyl)amide, a compound of claim 1.

13. (5E)-(16RS)-16,20-Dimethyl-18,18,19,19-tetradehydro-6a-carbaprostaglandin $I_2$ (2,3-dihydroxypropyl)amide a compound of claim 1.

14. (5E)-20-Methyl-18,18,19,19-tetradehydro-16,16-trimethylene-6a-carbaprostaglandin $I_2$ (2,3-dihydroxypropyl)amide, a compound of claim 1.

15. (5E)-13,14-Didehydro-20-methyl-18,18,19,19-tetradehydro-16,16-trimethylene-6a-carbaprostaglandin $I_2$ (2,3-dihydroxypropyl)amide, a compound of claim 1.

16. (5E)-(16RS)-16,19-Dimethyl-18,19-didehydro-6a-carbaprostaglandin $I_2$ (2,3-dihydroxypropyl)amide, a compound of claim 1.

17. (5E)-(16RS)-16-Methyl-18,18,19,19-tetradehydro-6a-carbaprostaglandin $I_2$ morpholide, a compound of claim 1.

18. A pharmaceutical composition comprising an amount of a compound of claim 1 effective to lower blood pressure and a pharmaceutically acceptable carrier.

19. A method of lowering blood pressure in a patient in need of such treatment, comprising administering to the patient an amount of a compound of claim 1 effective for such treatment.

* * * * *